(12) United States Patent
Roncali et al.

(10) Patent No.: US 7,731,796 B2
(45) Date of Patent: Jun. 8, 2010

(54) NITROGEN SEMICONDUCTOR COMPOUND AND DEVICE FABRICATED USING THE SAME

(75) Inventors: Jean Roncali, Angers (FR); Antonio Cravino, Angers (FR); Philippe Leriche, Angers (FR); Pierre Frere, Angers (FR); Sophie Roquet, Angers (FR)

(73) Assignee: Samsung Electronics Co., Ltd. (KR)

( * ) Notice: Subject to any disclaimer, the term of this patent is extended or adjusted under 35 U.S.C. 154(b) by 1040 days.

(21) Appl. No.: 11/362,035

(22) Filed: Feb. 27, 2006

(65) Prior Publication Data

US 2007/0068450 A1    Mar. 29, 2007

(30) Foreign Application Priority Data

Sep. 27, 2005    (KR) .................. 10-2005-0089797

(51) Int. Cl.
- C30B 25/00 (2006.01)
- C30B 28/14 (2006.01)
- H01L 23/52 (2006.01)
- H01L 29/40 (2006.01)

(52) U.S. Cl. .................. 117/89; 117/82; 117/83; 117/84; 117/85; 117/86; 117/87; 117/88; 257/774; 257/773; 257/784; 257/347

(58) Field of Classification Search ............ 117/82–89; 257/774, 773, 784, 347
See application file for complete search history.

(56) References Cited

U.S. PATENT DOCUMENTS

| | | | | |
|---|---|---|---|---|
| 6,001,284 | A * | 12/1999 | Enokida et al. | 252/583 |
| 6,369,258 | B1 * | 4/2002 | Ueda et al. | 556/487 |
| 6,696,588 | B2 * | 2/2004 | Ueda et al. | 556/487 |
| 6,830,832 | B2 * | 12/2004 | Oguma et al. | 428/690 |
| 7,126,153 | B2 * | 10/2006 | Iechi et al. | 257/40 |
| 7,223,641 | B2 * | 5/2007 | Maekawa | 438/149 |
| 7,244,515 | B2 * | 7/2007 | Doi et al. | 428/690 |
| 7,258,932 | B2 * | 8/2007 | Noguchi et al. | 428/690 |
| 7,420,204 | B2 * | 9/2008 | Iechi et al. | 257/40 |
| 2007/0068450 | A1 * | 3/2007 | Jung et al. | 117/89 |
| 2009/0056811 | A1 * | 3/2009 | Noguchi et al. | 136/263 |

OTHER PUBLICATIONS

Triphenylamine-Thienylenevinylene Hybrid Systems with Internal Charge Transfer as Donor Materials for Heterojunction Solar Cells Sophie Roquet, Antonio Cravino, Philippe Leriche, Olivier Alvque, Pierre Frre, and Jean Roncali J. Am. Chem. Soc., 2006, 128 (10), 3459-3466• DOI: 10.1021/ja058178e • Publication Date (Web): Feb. 18, 2006.*

(Continued)

Primary Examiner—G. Nagesh Rao
(74) Attorney, Agent, or Firm—Cantor Colburn LLP

(57) ABSTRACT

Disclosed herein are a novel nitrogen semiconductor compound simultaneously including groups with different electrical properties and a device fabricated using the nitrogen semiconductor compound as an organic semiconductor material or a hole conducting material. The nitrogen semiconductor compound can be spin-coated at room temperature when applied to the fabrication of the device, and has superior electrical conductivity and photovoltaic properties.

3 Claims, 2 Drawing Sheets

OTHER PUBLICATIONS

Synthesis andphotovoltaicpropertiesofastar-shapedmoleculewith triphenylamineascoreandbenzo[1,2,5]thiadiazolvinyleneasarms Guanglong Wu, GuangjinZhao, ChangHe, JingZhang, QingguoHe, Xiaomin Chen, YongfangLi, Solar EnergyMaterials&SolarCells 93(2009)108-113.*

David J. Brennan et al., Polyfluorenes as Organic Semiconductors for Polymeric Field Effect Transistors, Mat. Res. Soc. Symp. Proc., 2003 Materials Research Society, pp. L6.1.1, vol. 771.

Sandrine Martin et al., Source/Drain Contacts in Organic Polymer Thin Film Transistors, Mat. Res. Soc. Symp. Proc., 2003 Materials Research Society, pp. L6.2.1, vol. 771.

Tommie W. Kelley et al, High Performances Organic Thin Film Transistors, Mat. Res. Soc. Symp. Proc., 2003 Materials Research Society, pp. L6 5.1, vol. 771.

Francis Garnieret al., Molecular Engineering of Organic Semiconductors: Design of Self-Assembly Properties in Conjugated Thiophene Oligomers, J. Am. Chem. Soc. 1993, pp. 8716-8721, vol. 115.

"Organic materials for electronic and optoelectronic devices"; Author: Yasuhiko Shirota; Journal of Materials Chemistry, 2000, vol. 10., pp. 1-25.

"Novel Triarylamine Dendrimers as a Hole-Transport Material with a Controlled Metal-Assembling Function"; Authors: Satoh, et al.; J.Am. Chem. Soc., 2003, vol. 125, pp. 8104-8105.

Examination Report for Application No. 06 254 082.8-1211; Ref. DK/G28343EP.

Examination Report for Application No. 06 254 082.8-1211; Ref. DK/G28343EP, Apr. 9, 2009.

* cited by examiner

NITROGEN SEMICONDUCTOR COMPOUND AND DEVICE FABRICATED USING THE SAME

BACKGROUND OF THE INVENTION

1. Field of the Invention

The present invention relates to a novel nitrogen semiconductor compound and a device fabricated using the semiconductor compound. More particularly, the present invention relates to a nitrogen compound simultaneously including groups with different electrical properties, i.e. at least one electron acceptor and at least one electron donor, in side chains of the compound, and a device fabricated using the nitrogen compound as an organic semiconductor material or a hole conducting material.

2. Description of the Related Art

Thin film transistors (TFTs) are representative devices fabricated using organic semiconductor compounds, and are generally composed of a substrate, a gate electrode, an insulating layer, source/drain electrodes, and a channel layer. Inorganic semiconductor materials, such as silicon (Si), have been commonly used as materials for channel layers of TFTs. However, with increasing demand for the manufacture of large-area, flexible displays at reduced costs, organic semiconductor materials are currently used as materials for channel layers, i.e. semiconductor layers, rather than inorganic semiconductor materials involving high costs and requiring high-temperature vacuum processes. Recently, studies on organic semiconductor materials for channel layers of OTFTs have been undertaken and the characteristics of the devices have been reported. Of these, a great deal of research is currently concentrated on low molecular weight and oligomer organic semiconductor materials, e.g., melocyanines, phthalocyanines, perylenes, pentacenes, C60, thiophene oligomers, and the like. Lucent Technologies Inc. and 3M Inc. have developed devices with charge carrier mobilities as high as 3.2-5.0 cm$^2$/Vs using a pentacene single crystal (*Mat. Res. Soc. Symp. Proc.* 2003, Vol. 771, L6.5.1~L6.5.11). In addition, CNRS, France, reported a device having a relatively high charge carrier mobility of 0.01~0.1 cm$^2$/Vs and a relatively high on/off current ratio ($I_{on}/I_{off}$ ratio) using an oligothiophene derivative (*J. Am. Chem. Soc.*, 1993, Vol. 115, pp. 8716-8721). However, since these materials are largely dependent on vacuum processes in order to form thin films, the fabrication of devices incurs considerable costs. Under such circumstances, research is underway on organic polymer semiconductor compounds that can be coated by spin coating.

On the other hand, as other devices where organic semiconductor materials are used, there are exemplified organic solar cells. General solar photovoltaic cells consist essentially of a semiconductor layer and electrodes. The operational principle of a solar photovoltaic cell is as follows. Externally incident light generates electrons and holes inside a semiconductor layer. The electrons and holes migrate toward positive (P) and negative (N) electrodes, respectively, to generate a potential difference between the two electrodes. When load is applied to the solar photovoltaic cell, electric current flows in the solar photovoltaic cell. As described above, there is a growing tendency to use organic semiconductor materials as materials for semiconductor layers of solar photovoltaic cells rather than inorganic semiconductor materials involving high costs and requiring high-temperature vacuum processes. Thus, there is a need to develop a semiconductor compound that can be applied to the fabrication of devices, particularly, solar photovoltaic cells, by spin coating without a reduction in the efficiency of the devices despite increasing light intensity.

SUMMARY OF THE INVENTION

Therefore, the present invention has been made in view of the above problems of the prior art, and it is an object of the present invention to provide a nitrogen compound simultaneously including groups with different electrical properties, i.e. at least one electron acceptor and at least one electron donor, in side chains of the compound, as an organic semiconductor compound that can be stably spin-coated at room temperature when applied to the fabrication of a device, as well as has superior electrical conductivity.

In accordance with one aspect of the present invention for achieving the above object, there is provided a nitrogen semiconductor compound represented by Formula 1 below:

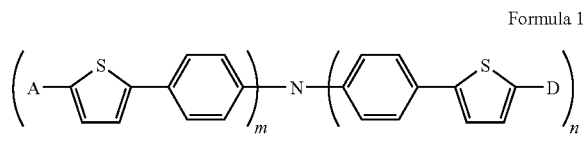

Formula 1 wherein A represents an electron acceptor, D represents an electron donor, m and n each is an integer of 1 or greater, and the sum of m and n is 3.

In accordance with another aspect of the present invention, there is provided a device fabricated using the nitrogen compound as an organic semiconductor material or a hole conducting material.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

The present invention will now be described in more detail with reference to the accompanying drawings.

The present invention provides a nitrogen semiconductor compound represented by Formula 1 below:

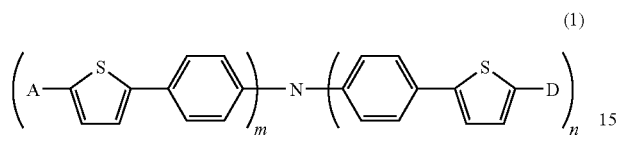

(1)

wherein A represents an electron acceptor, D represents an electron donor, m and n each is an integer of 1 or greater, and the sum of m and n is 3.

Figure 1:
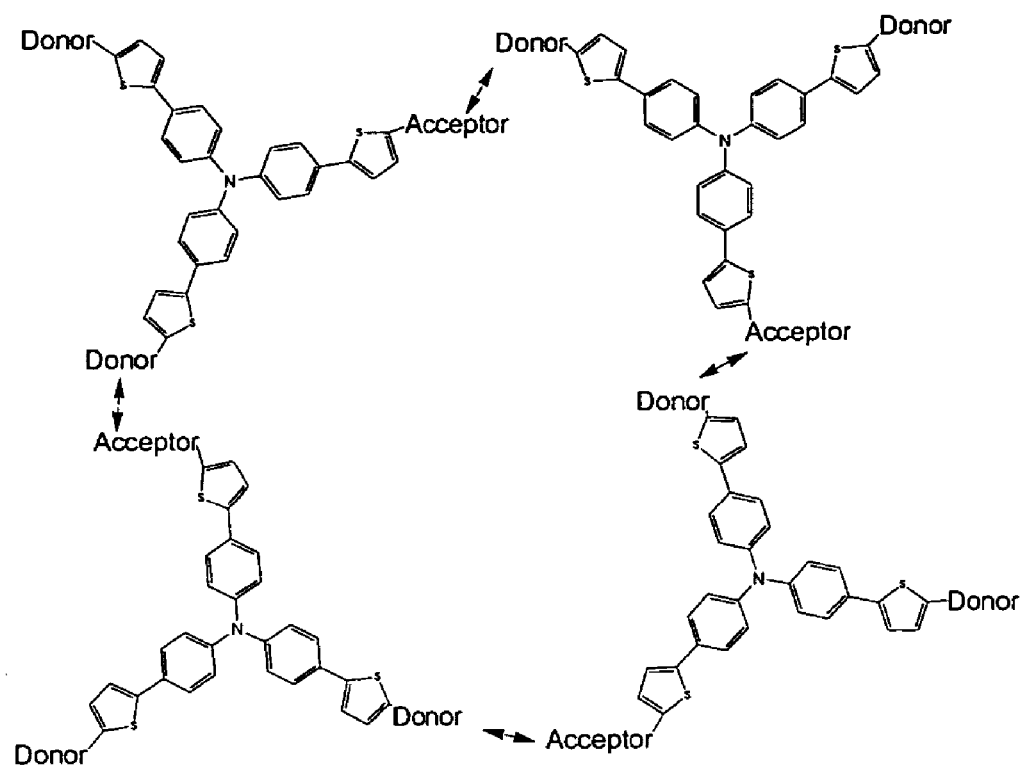
FIG. 1 is a diagram schematically showing the electron donor-acceptor interaction between nitrogen semiconductor compounds according to the present invention.

Specifically, the nitrogen compound of the present invention includes one central nitrogen atom, at least one electron acceptor, and at least one electron donor. Although the nitrogen compound of the present invention has a low molecular weight, it has a constant oxidation potential and is superior in stability due to its structure when applied to the fabrication of devices. Further, when several molecules of the compound are present, they interact with each other as shown in FIG. 1, facilitating formation of a solution. One molecule of the nitrogen compound including at least one group (i.e. electron donor) having a strong tendency to provide electrons and at least one group (i.e. electron acceptors) having a strong tendency to receive the electrons is arranged adjacent to another molecule of the compound due to the electrical properties of the electron acceptors and donors. In this manner, several molecules of the nitrogen compound gather together and act as one polymer compound, thus achieving superior electrical properties.

More specifically, the electron acceptor A in the compound of Formula 1 can be represented by any one of Formulae 2 to 4 below:

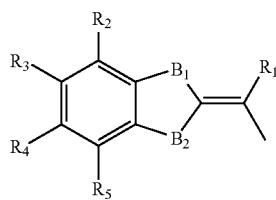

Formula 2 wherein $R_1$, $R_2$, $R_3$, $R_4$, and $R_5$ are each independently a hydrogen atom, a halogen atom, —CN, a $C_{1-12}$ linear or branched alkyl group, a $C_{1-12}$ linear or branched alkoxy group, or a $C_{1-12}$ linear or branched alkoxyalkyl group, and $B_1$ and $B_2$ are each independently

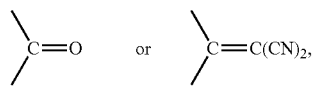

of which may be —O—;

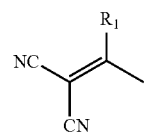

Formula 3 wherein $R_1$ is as defined in Formula 2; and

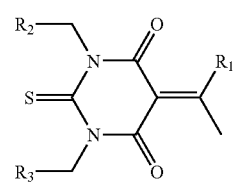

Formula 4 wherein $R_1$, $R_2$, and $R_3$ are as defined in Formula 2.

Meanwhile, the electron donor D in the compound of Formula 1 can be represented by any one of Formulae 5 to 8 below:

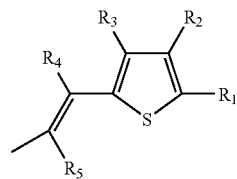

Formula 5 wherein $R_1$, $R_2$, $R_3$, $R_4$, and $R_5$ are each independently a hydrogen atom, a $C_{1-12}$ linear or branched alkyl group, a $C_{1-10}$ linear or branched alkoxy group, or a $C_{1-10}$ alkoxyalkyl group;

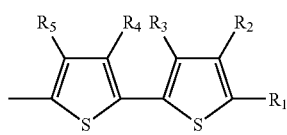

Formula 6 wherein $R_1$, $R_2$, $R_3$, $R_4$, and $R_5$ are as defined in Formula 5;

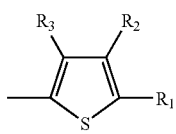

Formula 7 wherein $R_1$, $R_2$, and $R_3$ are as defined in Formula 5; and

Formula 8

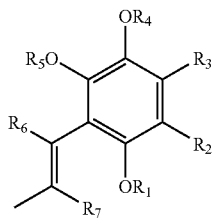

wherein $R_1$, $R_2$, $R_3$, $R_4$, $R_5$, $R_6$, and $R_7$ are each independently a hydrogen atom, a $C_{1-12}$ linear or branched alkyl group, a $C_{1-10}$ linear or branched alkoxy group, or a $C_{1-10}$ alkoxyalkyl group.

The nitrogen compound of the present invention has a low molecular weight of from 600 to 2,000.

More specific examples of nitrogen compounds that can include both the electron acceptor and the electron donor are the compounds of Formulae 9 to 13 below:

Formula 9

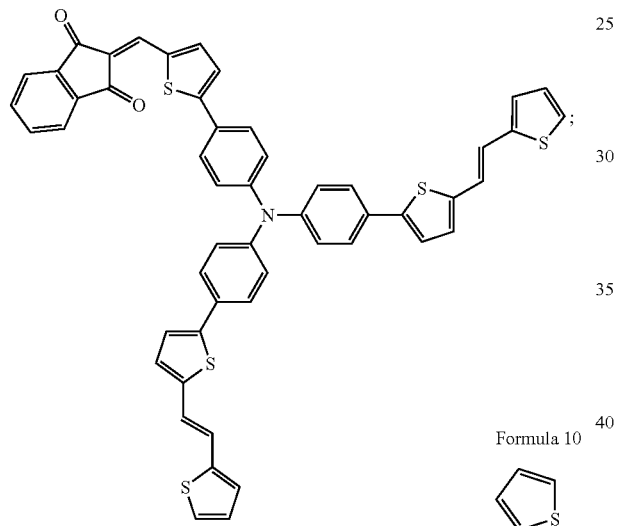

Formula 10

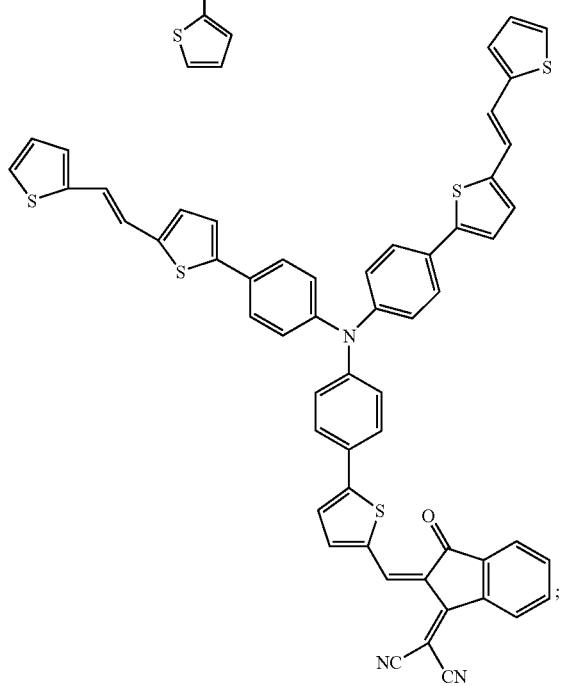

Formula 11

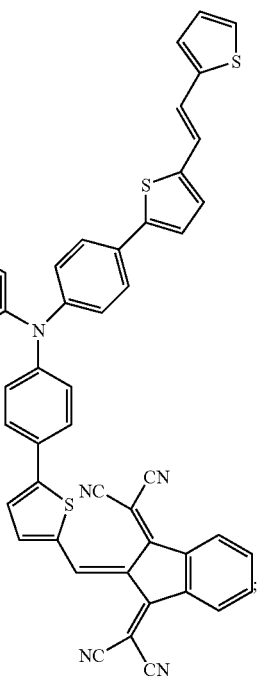

Formula 12

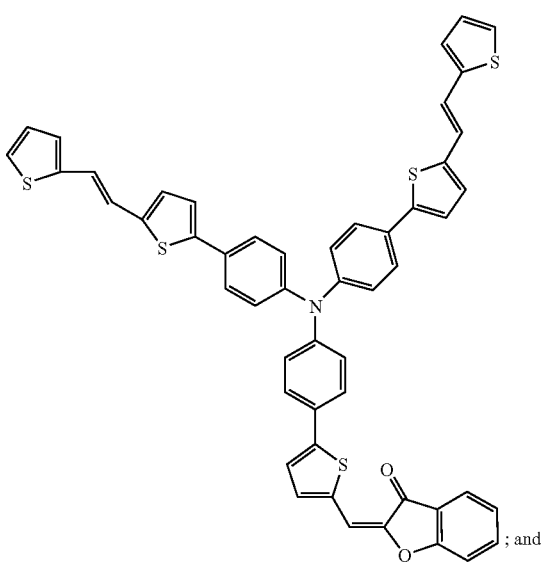

; and

Formula 13

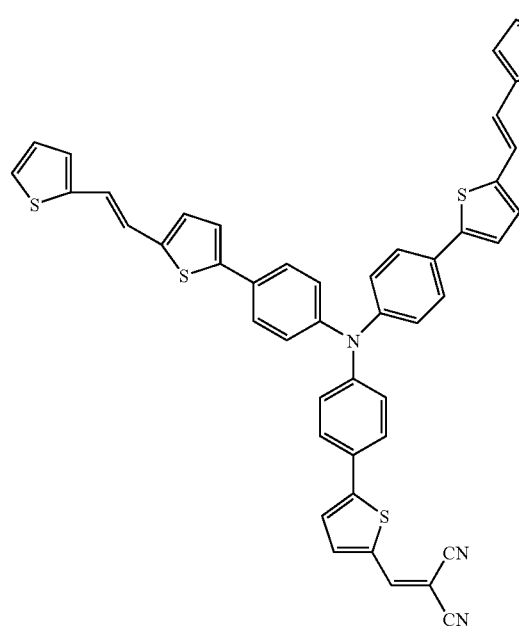

These compounds have a structure wherein two dithienylenevinylene groups as electron donors and one indanedione group as an electron acceptor are bonded to one central nitrogen atom of the molecule through phenylene and thiophene as linking groups. If necessary, the nitrogen compound of the present invention may include one dithienylenevinylene group and two indanedione groups.

The nitrogen semiconductor compound of Formula 1 according to the present invention can be synthesized, without limitation, by methods known in the art. For example, the compound of Formula 9 can be synthesized by the following Reactions 1 and 2:

Reaction 1

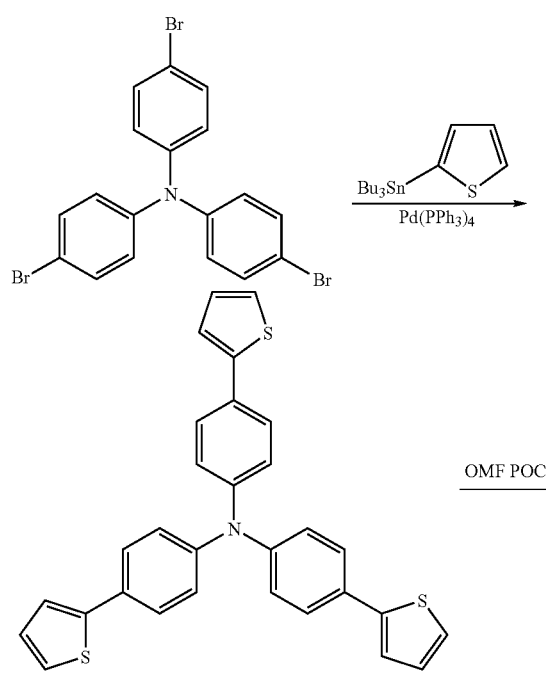

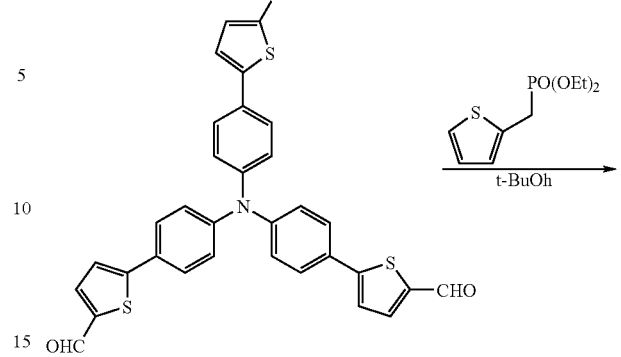

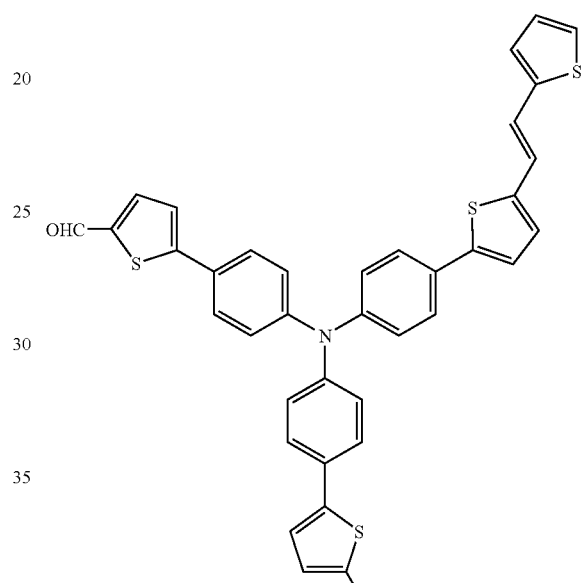

Reaction 2

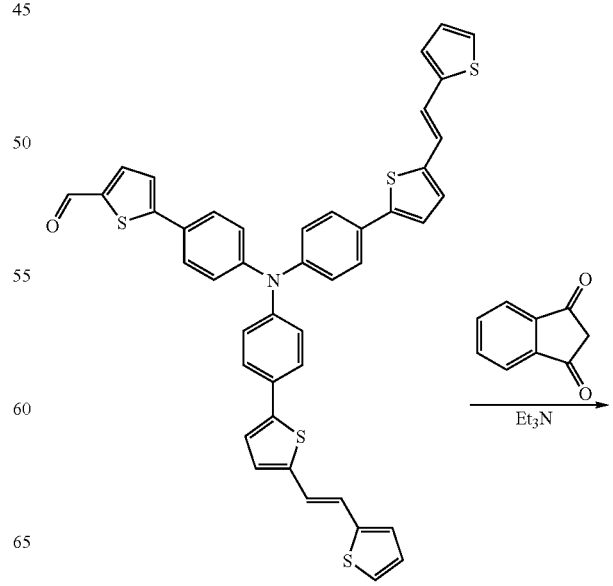

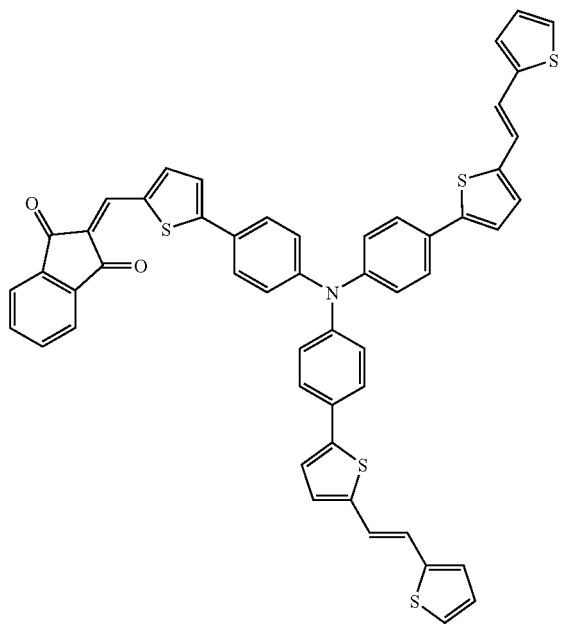

Reaction 1 and 2 are preferably performed by refluxing in chloroform, dichloromethane, or the like, under a nitrogen atmosphere for 8~14 hours in the presence of an excess of an amine, e.g., triethylamine, as a base.

As is apparent from the synthetic routes, if necessary, various groups having electron accepting and electron donating properties may be bonded to the nitrogen compounds. Accordingly, the substituents of the nitrogen compounds according to the present invention can be controlled in order to facilitate formation of a solution when the nitrogen compounds can be applied to the fabrication of devices. As a result, the nitrogen semiconductor compounds can be coated at room temperature by already known coating techniques. Specifically, the nitrogen semiconductor compounds can be formed into a thin film having a desired thickness by screen printing, printing, spin coating, spin casting, dipping, and ink spraying.

The present invention also provides a device fabricated using the nitrogen compound as an organic semiconductor material or a hole conducting material.

Specific examples of the device according to the present invention include organic thin film transistors (OTFTs), organic field effect transistors (OFETS), organic solar photovoltaic cells, and organic light emitting devices.

The nitrogen compound of the present invention can be used as a material for an organic semiconductor layer of an OTFT or OFET, or as a hole conducting material of an organic solar photovoltaic cell or an organic light emitting device by processes known in the art.

The present invention will now be described in more detail with reference to the following examples. However, these examples are given for the purpose of illustration and are not to be construed as limiting the scope of the invention.

Preparative Example 1

Preparation of Nitrogen Semiconductor Compound (1)

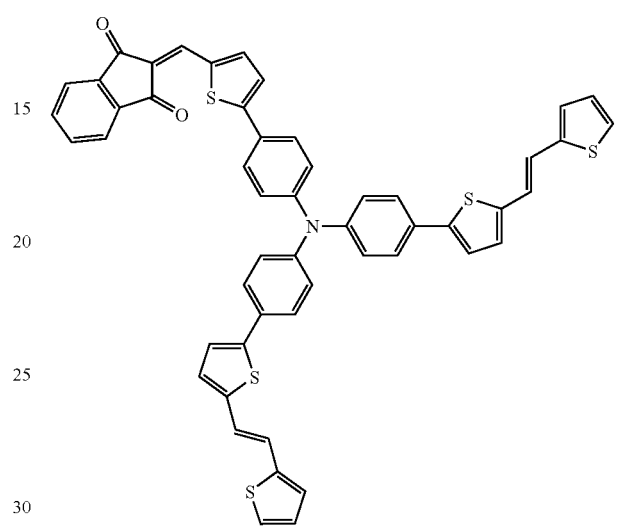

The above nitrogen semiconductor compound was synthesized by the following reactions:

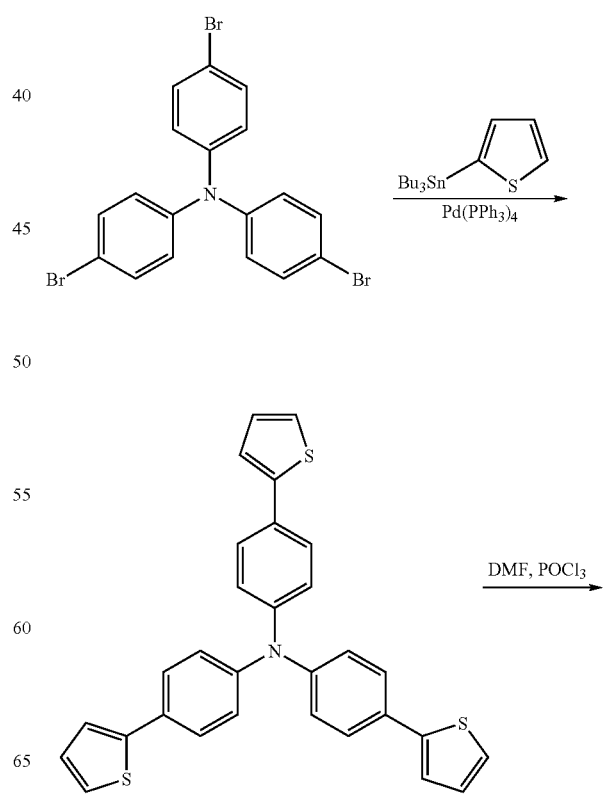

-continued

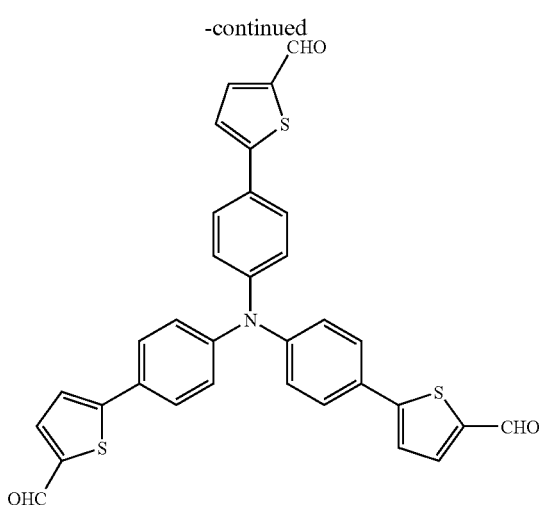

First, 1 g (2 mmol) of tris(4-bromophenyl)amine (Aldrich) was dissolved in 100 ml of toluene, and then 2.9 ml (4.5 eq.) of 2-tributylstannylthiophene and 27 mg (1.1%) of Pd(PPh$_3$)$_4$ were added thereto. The mixture was refluxed under a nitrogen atmosphere for 12 hours. The reaction mixture was allowed to cool to room temperature, washed with brine twice, and dried over MgSO$_4$. After the solvent was evaporated, the obtained residue was washed with petroleum ether (PE), and dried, affording 0.87 g (yield: 85%) of tris[4-(2-thienyl)phenyl]amine as a pale yellow solid.

$^1$H NMR (CDCl$_3$) δ (ppm): 7.50 (d, 2H) 7.20 (m, 2H) 7.10 (d, 2H) 7.08 (dd, 1H)

500 mg (1 mmol) of the tris[4-(2-thienyl)phenyl]amine was dissolved in 30 ml of 1,2-dichloroethane and DMF (0.37 g), and then 0.78 g (5 eq.) of POCl$_3$ was added thereto. The mixture was refluxed under a nitrogen atmosphere for 15 hours. To the reaction mixture were added 50 ml of methylene chloride and 100 ml of a saturated aqueous sodium acetate solution. The resulting mixture was stirred for 2 hours. The obtained organic phase was separated, washed with water, and dried over MgSO$_4$. The solvents were evaporated, and then the residue was purified by column chromatography, affording 0.53 g (yield: 90%) of tris[4-(5-formyl-2-thienyl)phenyl]amine as an orange solid.

$^1$H NMR (CDCl$_3$) δ (ppm): 9.90 (s, 1H, CHO) 7.70 (d, 1H) 7.60 (d, 1H) 7.30 (d, 2H) 7.20 (d, 2H)

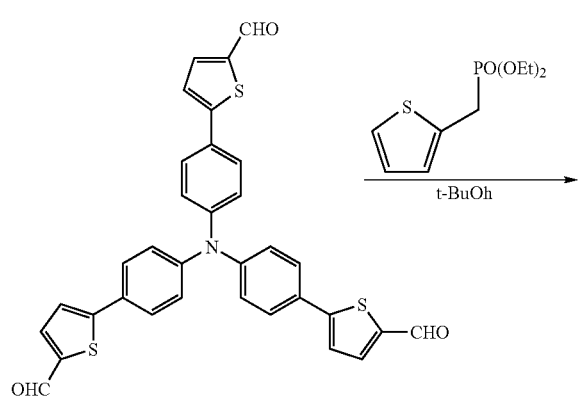

-continued

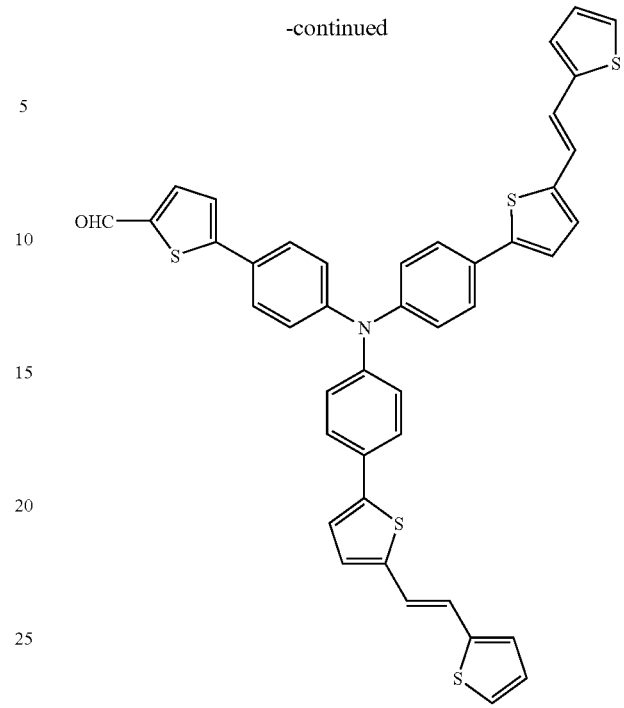

400 mg (0.7 mmol) of the tris[4-[5-fomyl-2-thienyl]phenyl]amine and 400 mg (2.5 eq) of the thienyl-2-methyldiethylphosphonate were dissolved in 50 ml of anhydrous THF, and then 191 mg (2.5 eq.) of calcium-t-butoxide was added thereto. The mixture was stirred under a nitrogen atmosphere at room temperature for 12 hours. To the reaction mixture were added 150 ml of dichloromethane. The obtained organic phase was washed with water, and dried over MgSO$_4$. After the solvent was evaporated, the obtained residue was washed with petroleum ether (PE), and dried. The solvents were evaporated, and then the residue was purified by column chromatography, affording 100 mg (yield: 20%) of bis(4-[5-(2-thienylethenyl)-2-thienyl]phenyl}-4-(5-formyl-2-thienyl)phenyl]amine as an orange solid.

$^1$H NMR (CDCl$_3$) δ (ppm): 9.90 (s, 1H, CHO) 7.70 (d, 1H) 7.60 (d, 2H) 7.50 (d, 4H) 7.35 (d, 1H) 7.20 (d, 2H), 7.15 (m, 8H) 7.00 (m, 10H)

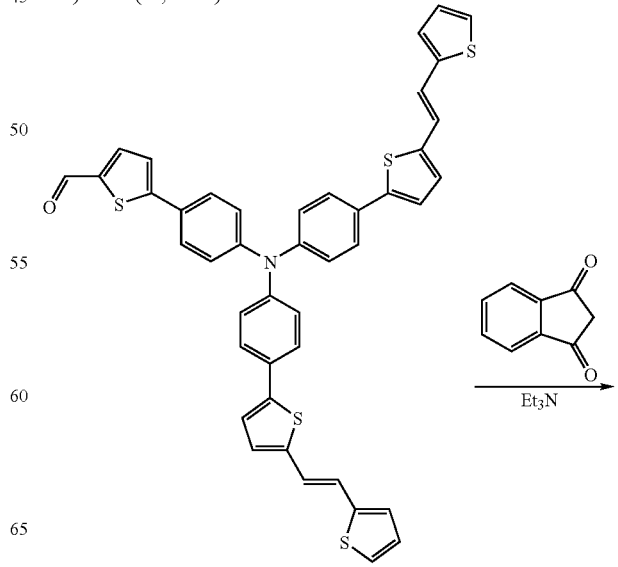

-continued

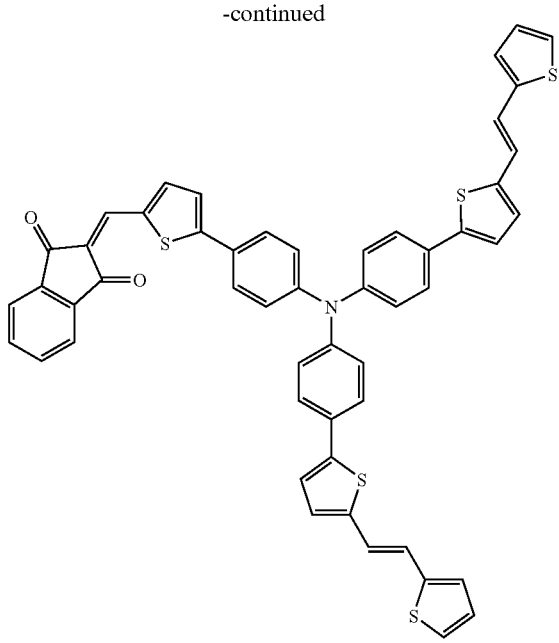

100 mg (0.1 mmol) of the bis(4-[5-(2-thienylethenyl)-2-thienyl]phenyl}-4-(5-formyl-2-thienyl)phenyl]amine was dissolved in 30 ml of chloroform, and then 30 ml (1.5 eq.) of indanedione and an excess of triethylamine were added thereto under a nitrogen atmosphere. After the mixture was refluxed under a nitrogen atmosphere for 12 hours, the reaction mixture was allowed to cool to room temperature. The obtained organic phase was washed with water, and dried over $MgSO_4$. The solvents were evaporated, and then the residue was purified by column chromatography, affording 50 mg (yield: 43%) of the final compound as a red solid.

$^1$H-NMR (CDCl$_3$) δ (ppm) 8.00 (m, 5H), 7.80 (m, 1H), 7.70 (d, 2H), 7.55 (d, 4H), 7.40 (d, 1H), 7.20 (m, 10H), 7.00 (m, 10H)

Figure 2:
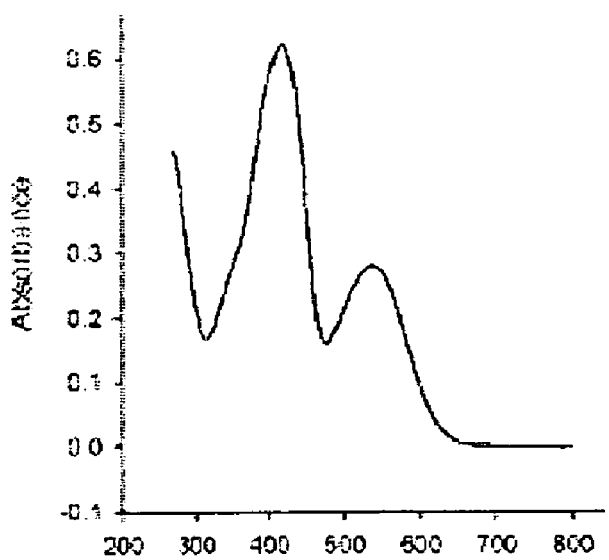
FIG. 2 is a UV absorption spectrum of a low molecular weight nitrogen compound synthesized in Preparative Example 1 of the present invention.

The UV absorbance of the final compound was measured, and the obtained results are shown in FIG. 2. The graph shown in FIG. 2 demonstrates that the nitrogen compound absorbs UV light at a broad range of wavelengths.

Example 1

Measurement of Photovoltaic Efficiency

Figure 3:
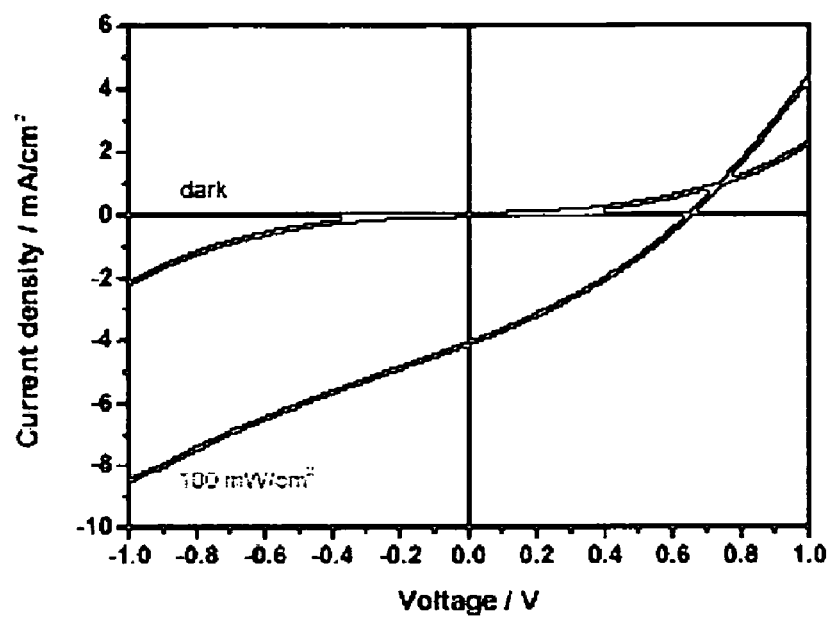
FIG. 3 is a graph showing the current-voltage (I-V) characteristics of a solar cell device fabricated in Example 1 of the present invention.
Figure 4:
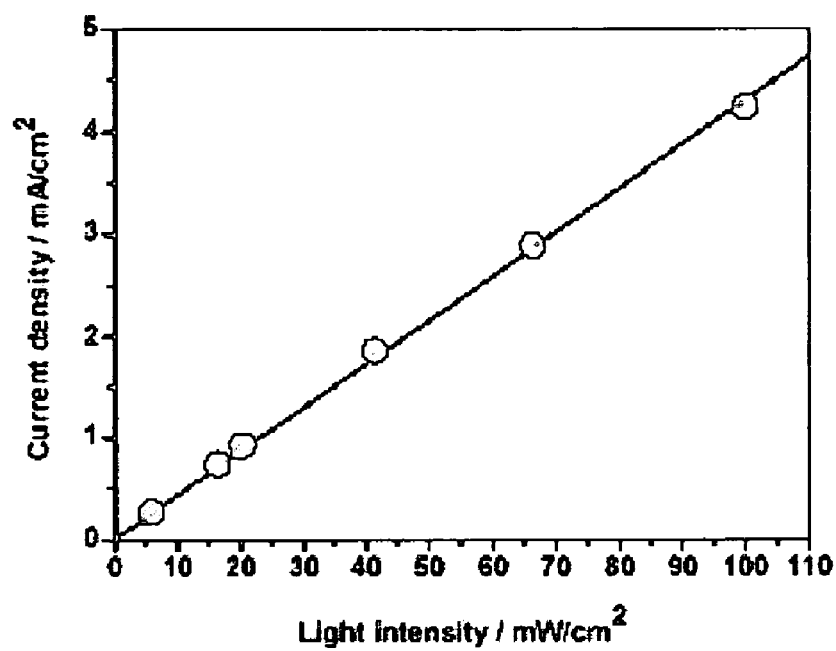
FIG. 4 is a graph showing the efficiency of a solar cell device fabricated in Example 1 of the present invention as a function of light intensity.

An ITO electrode was formed on a glass substrate, and then an 80 nm-thick layer of a conductive polymer (Baytron P, Bayer) was formed thereon. Thereafter, a mixture of the nitrogen semiconductor compound synthesized in Preparative Example 1 and [6,6]-phenyl-C$_{61}$-butyric acid methylester (PCBM) (1:3 (w/w)) was spin-cast on the conductive polymer layer to form a 100 nm-thick organic semiconductor layer. Then, a 60 nm-thick counter electrode made of aluminum was formed on the organic semiconductor layer to fabricate a device for the measurement of photovoltaic efficiency. The current-voltage characteristics were measured under AM 1.5 illumination conditions, and the results are plotted in FIG. 3. The photovoltaic efficiency of the device was measured to be 0.84% at a light intensity of 100 mW/cm$^2$, as calculated from FIG. 3. Further, to evaluate the efficiency of the device as a function of light intensity, changes in the current density of the device were measured according to the changes in light intensity using a solar simulator under 1 sun AM 1.5 illumination conditions. The results are plotted in FIG. 4. As shown in FIG. 4, the current density of the device was increased linearly with increasing light intensity, which indicates that the device of the present invention shows characteristics suitable for a solar cell.

As apparent from the above description, the novel nitrogen compound of the present invention is a stable low molecular weight semiconductor compound, can be spin-coated at room temperature, and has superior electrical conductivity. Therefore, the nitrogen semiconductor compound of the present invention can be widely applied to the fabrication of organic thin film transistors (OTFTs), organic field effect transistors (OFETs), organic solar photovoltaic cells, and organic light emitting devices by relatively simple processes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A nitrogen semiconductor compound represented by Formula 1 below:

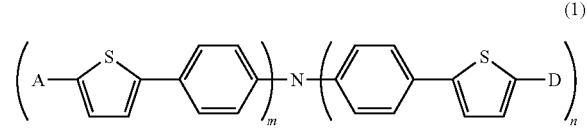

(1)

wherein A represents an electron acceptor, D represents an electron donor, m and n each is an integer of 1 or greater, and the sum of m and n is 3.

2. The nitrogen semiconductor compound according to claim 1, wherein the electron acceptor A is represented by any one of Formulae 2 to 4 below:

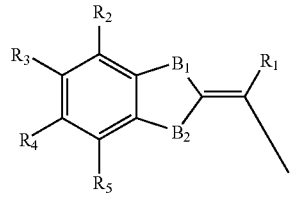

(2)

wherein $R_1$, $R_2$, $R_3$, $R_4$, and $R_5$ are each independently a hydrogen atom, a halogen atom, —CN, a $C_{1-2}$ linear or branched alkyl group, a $C_{1-12}$ linear or branched alkoxy group, or a $C_{1-12}$ linear or branched alkoxyalkyl group, and $B_1$ and $B_2$ are each independently

or

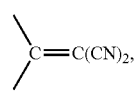

one of which may be —O—,

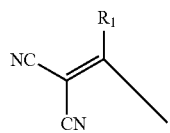 (3)

wherein R$_1$ is as defined in Formula 2, and

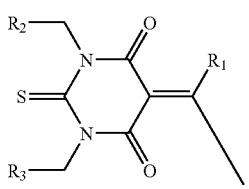 (4)

wherein R$_1$, R$_2$, and R$_3$ are as defined in Formula 2; and the electron donor D is represented by any one of Formulae 5 to 8 below:

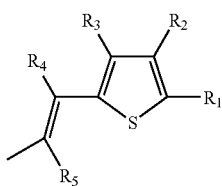 (5)

wherein R$_1$, R$_2$, R$_3$, R$_4$, and R$_5$ are each independently a hydrogen atom, a C$_{1-12}$ linear or branched alkyl group, a C$_{1-10}$ linear or branched alkoxy group, or a C$_{1-10}$ alkoxyalkyl group,

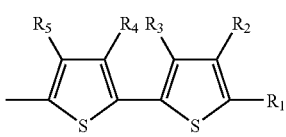 (6)

wherein R$_1$, R$_2$, R$_3$, R$_4$, and R$_5$ are as defined in Formula 5,

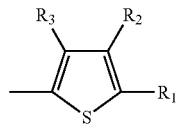 (7)

wherein R$_1$, R$_2$, and R$_3$ are as defined in Formula 5, and

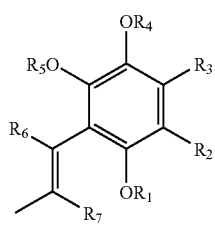 (8)

wherein R$_1$, R$_2$, R$_3$, R$_4$, R$_5$, R$_6$, and R$_7$ are each independently a hydrogen atom, a C$_{1-12}$ linear or branched alkyl group, a C$_{1-10}$ linear or branched alkoxy group, or a C$_{1-10}$ alkoxyalkyl group.

3. The nitrogen semiconductor compound according to claim 1, wherein the compound of Formula 1 is selected from the group consisting of the compounds of Formulae 9 to 13 below:

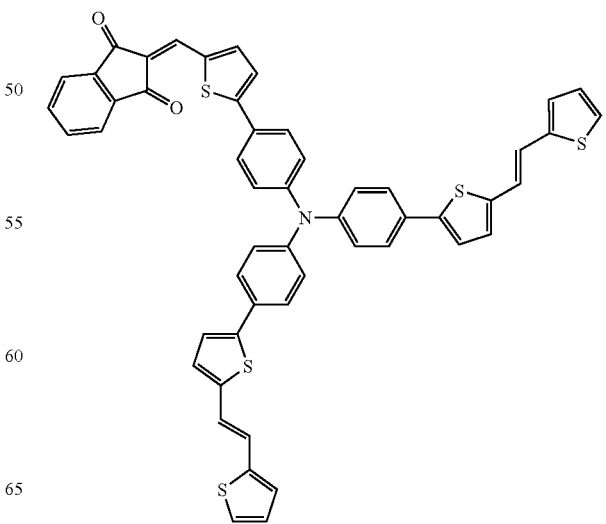 (9)

(10)
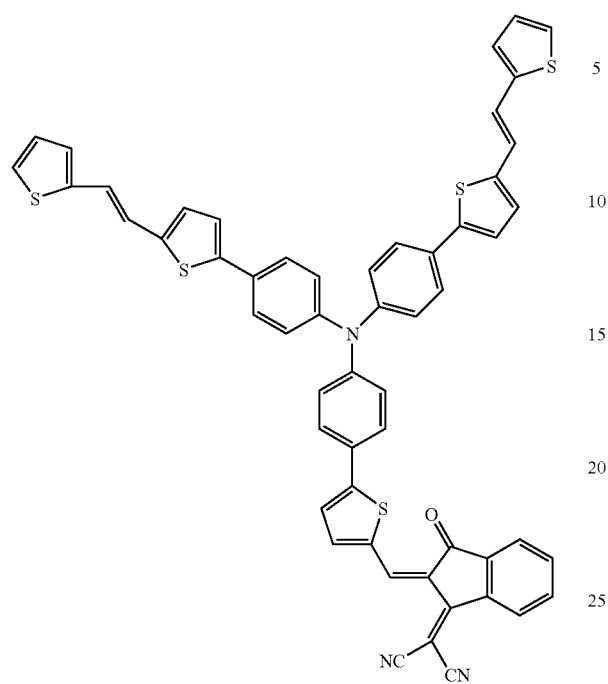
(11)
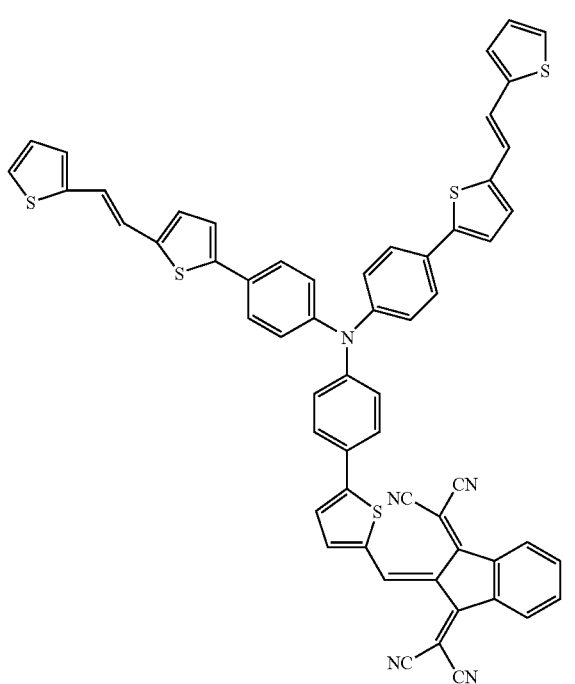
(12)
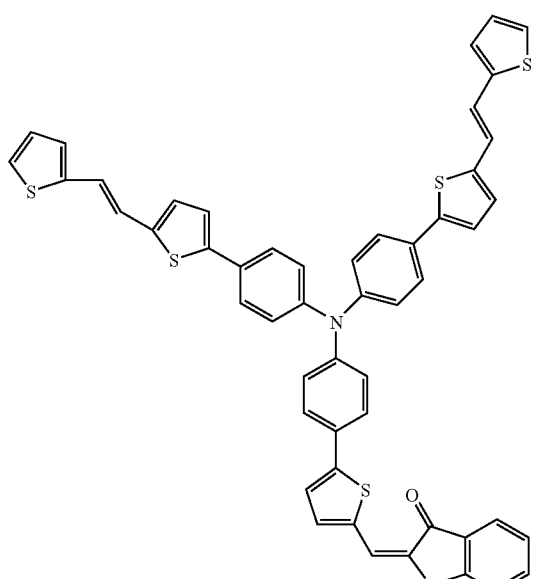
(13)
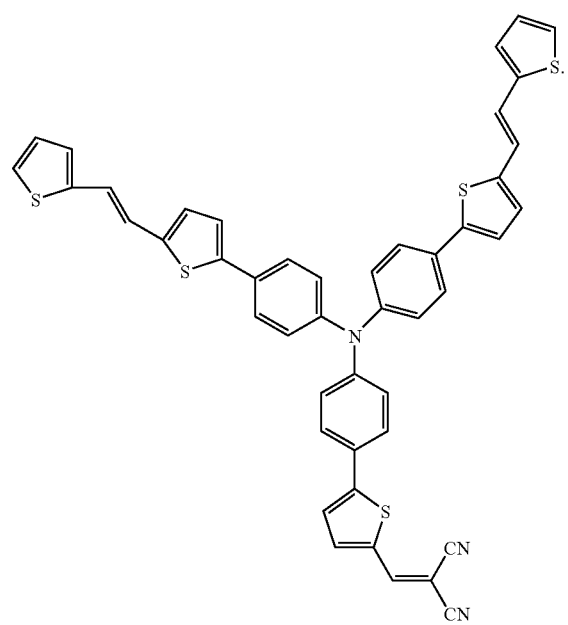
* * * * *